United States Patent
Hsieh et al.

(10) Patent No.: US 10,663,779 B1
(45) Date of Patent: May 26, 2020

(54) WELDING HELMET WITH SINGLE LCD FILTER LENS

(71) Applicant: ARCMASK OPTECH CO., LTD, Taoyuan (TW)

(72) Inventors: Chien-Hsing Hsieh, Taoyuan (TW); Edward Martin, Tanuton, MA (US); Chia-Hung Chen, Taoyuan (TW); James Watkins, Tanuton, MA (US)

(73) Assignee: ARCMASK OPTECH CO., LTD., Taoyuan (TW)

( * ) Notice: Subject to any disclaimer, the term of this patent is extended or adjusted under 35 U.S.C. 154(b) by 0 days.

(21) Appl. No.: 16/507,431

(22) Filed: Jul. 10, 2019

(51) Int. Cl.
  *G02F 1/133* (2006.01)
  *A61F 9/06* (2006.01)

(52) U.S. Cl.
  CPC ............ *G02F 1/13318* (2013.01); *A61F 9/06* (2013.01); *A61F 9/067* (2013.01); *G02F 1/13306* (2013.01); *G02F 2001/13324* (2013.01)

(58) Field of Classification Search
  None
  See application file for complete search history.

(56) References Cited

U.S. PATENT DOCUMENTS

2018/0360663 A1* 12/2018 Hsieh ................ A61F 9/067

* cited by examiner

*Primary Examiner* — Phu Vu
(74) *Attorney, Agent, or Firm* — Thomas J. Nikolai; DeWitt LLP

(57) ABSTRACT

A welding helmet includes a helmet shell and a lens device mounted on the helmet shell. The lens device includes a filter control module and a single LCD panel. The logic control module controls the transmittance of the single LCD panel based on a sensed light signal and a shading-level signal designated by a user. Therefore, when the welding helmet is operated in an environment having intense light such as a welding arc, the single LCD panel will turn dark and lower its transmittance to block the intense light.

9 Claims, 7 Drawing Sheets

WELDING HELMET WITH SINGLE LCD FILTER LENS

BACKGROUND OF THE INVENTION

1. Field of the Invention

The present invention relates to a welding helmet, and particularly to a welding helmet having a single liquid crystal display (LCD) filter lens capable of automatically adjusting transmittance to protect human eyes from the glare.

2. Description of the Related Art

A welder may wear a welding helmet when working. The welding helmet may protect the eyes, face, and neck of the welder from flash burn, ultraviolet light, sparks, infrared light, and heat.

The welding helmet is equipped with a dark lens, and the welder may clearly see a welding position through the dark lens. However, when the welder is not working, the welder may not clearly see the surroundings through the dark lens. Hence, the welder may take off the welding helmet from a position in front of the eyes to clearly see the surroundings.

Another conventional welding helmet may have a viewing lens with a function of automatically adjusting light transmittance. Therefore, the welder wearing the welding helmet can still clearly see the surroundings through the viewing lens that automatically turns to have a higher light transmittance.

However, the conventional viewing lens are composed of two LCD panels stacked to each other. A relatively complex and high-cost control circuit is needed to control operations of the two LCD panels.

SUMMARY OF THE INVENTION

An objective of the present invention is to provide a welding helmet using one single LCD filter lens to filter or block welding arcs.

To achieve the foregoing objective, the welding helmet includes a helmet shell and a lens device. The helmet shell includes a mounting hole. The lens device is mounted in the mounting hole of the helmet shell.

The lens device comprises a solar panel generating electric power, a light sensor generating a light signal corresponding to ambient light of the welding helmet, multiple selection switches for generating different shading-level signals respectively, wherein one of the multiple selection switches is selected to generate a designated shading-level signal, and a filter control unit electrically connected to the solar panel, the light sensor and the multiple selection switches.

The filter control unit comprises a battery connected to the solar panel and storing the electric power, a logic control module receiving the light signal and the designated shading-level signal, a DC to AC module controlled by the logic control module to output a control signal, and a single LCD display filter lens comprising a single LCD panel electrically connected to the DC to AC module and transmittance of the single LCD panel being determined by the control signal.

When the logic control module determines that the light signal is lower than a threshold, the DC to AC module outputs a zero-voltage signal to the single LCD panel and the single LCD panel is transparent.

When the logic control module determines that the light signal exceeds the threshold, the logic control module controls the DC to AC module to generate the control signal corresponding to the designated shading-level signal to lower the transmittance of the single LCD panel to a level for blocking the ambient light.

The peak amplitude of the control signal is between 6 and 25 volts and a frequency of the control signal is in a range between 0.01 and 1 Hz.

Other objectives, advantages and novel features of the invention will become more apparent from the following detailed description when taken in conjunction with the accompanying drawings.

BRIEF DESCRIPTION OF THE DRAWINGS

FIG. 7C shows a zero-voltage signal applied to the LCD panel.

DETAILED DESCRIPTION OF THE INVENTION

Figure 1:
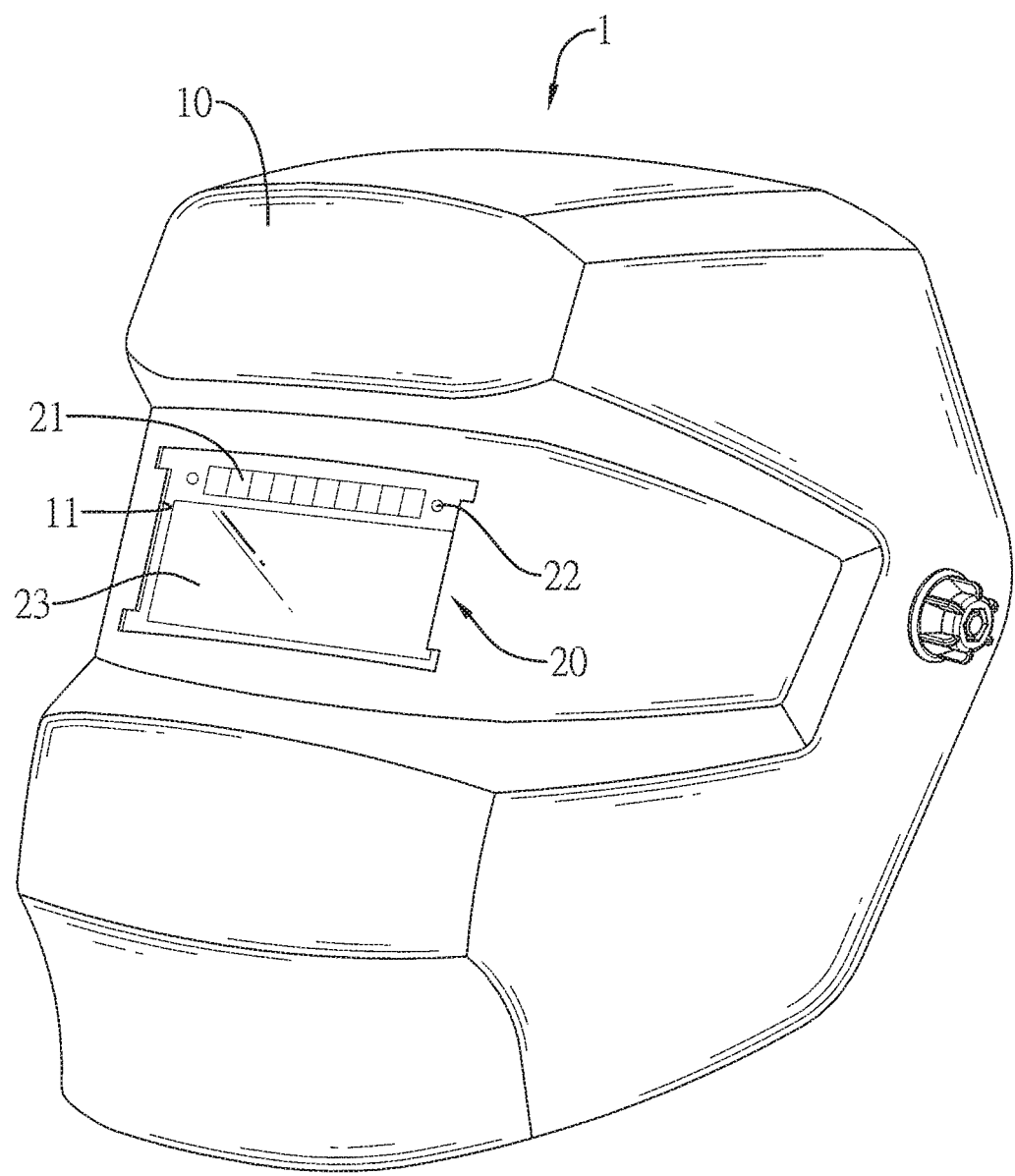
FIG. 1 is a schematic view of a welding helmet of the present invention.

With reference to FIG. 1, a welding helmet 1 in accordance with the present invention includes a helmet shell 10 and a lens device 20. The helmet shell 10 includes a mounting hole 11. The lens device 20 is mounted in the mounting hole 11 of the helmet shell 10 and has an outer surface 201 and an inner surface 202.

Figure 2:
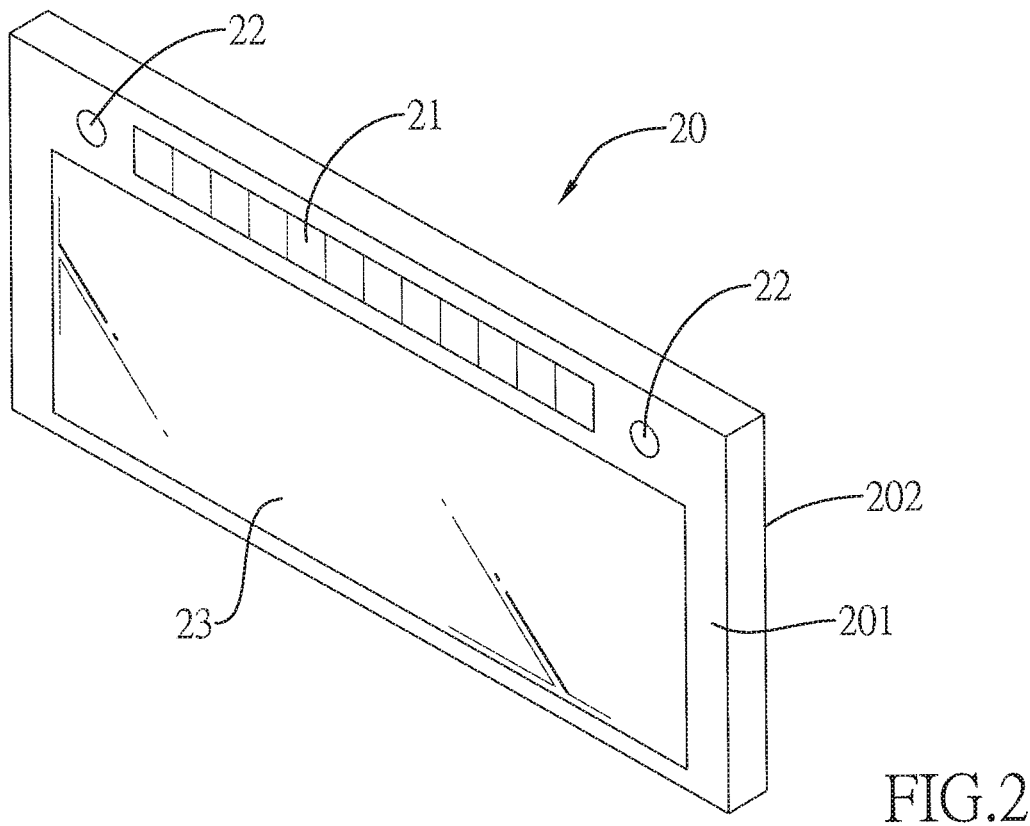
FIG. 2 is a front schematic view of a lens device for the welding helmet of FIG. 1.
Figure 3:
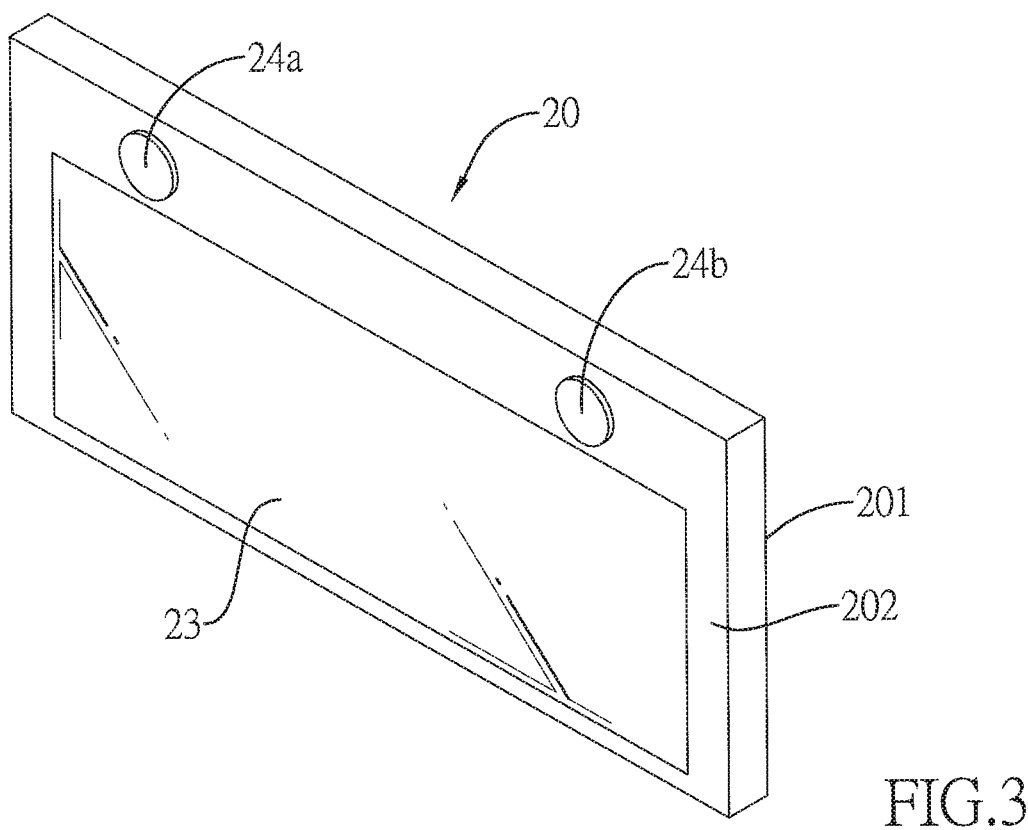
FIG. 3 is a rear schematic view of the lens device of FIG. 2.
Figure 4:
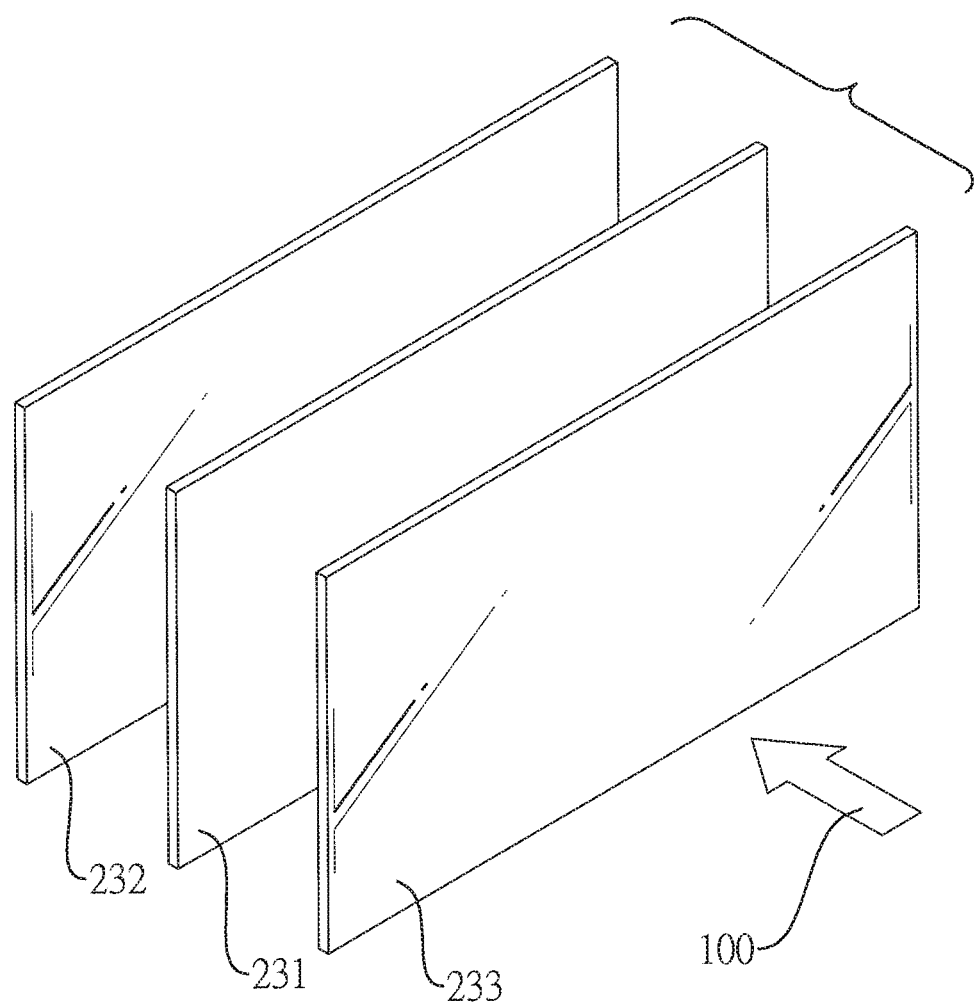
FIG. 4 is a schematic view of an LCD filter lens shown in FIGS. 2 and 3.

With reference to FIGS. 2 to 4, the lens device 20 comprises a solar panel 21, a light sensor 22, a single liquid crystal display (LCD) filter lens 23, multiple selection switches 24a, 24b and a filter control unit 25.

The solar panel 21 is mounted on the outer surface 201 of the lens device 20 and generates electric power and transmits the electric power to the filter control unit 25.

The light sensor 22 is mounted on the outer surface 201 of the lens device 20 and senses ambient light such as a welding arc to generate and transmit a light signal to the filter control unit 25.

The LCD filter lens 23 is a high-impedance LCD lens. The LCD filter lens 23 comprises a single LCD panel 231, an inner glass 232 and an outer glass 233. The inner glass 232 and the outer glass 233 may be respectively attached at two opposite surfaces of the LCD panel 231 as shown in FIG. 4. The inner glass 232 may be a clear glass. The outer glass 233 faces outward and is a reflective glass for reflecting ultraviolet radiation and infrared radiation of the welding arc 100. The LCD panel 231 is electrically connected to and controlled by the filter control unit 25.

The multiple selection switches 24a, 24b are mounted on the inner surface 202 of the lens device 20 and electrically connected to the filter control unit 25. The selection switches 24a, 24b are manipulated by a user to generate different shading-level signals respectively. In this embodiment, there are two selection switches 24a, 24b, i.e. the first selection switch 24a and the second selection switch 24b for respectively generating a first shading-level signal and a second shading-level signal.

Figure 5:
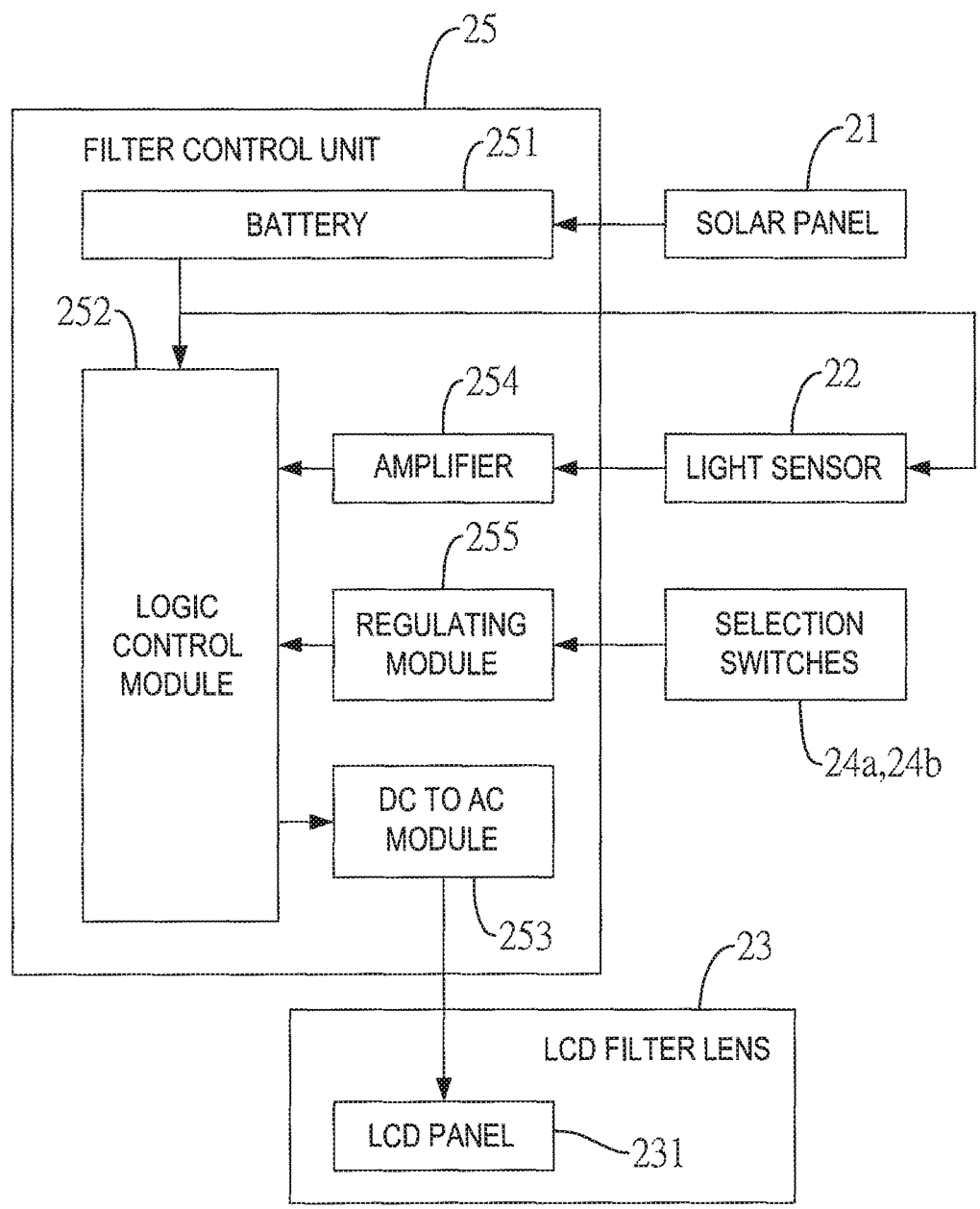
FIG. 5 is a block diagram of the lens device.
Figure 6:
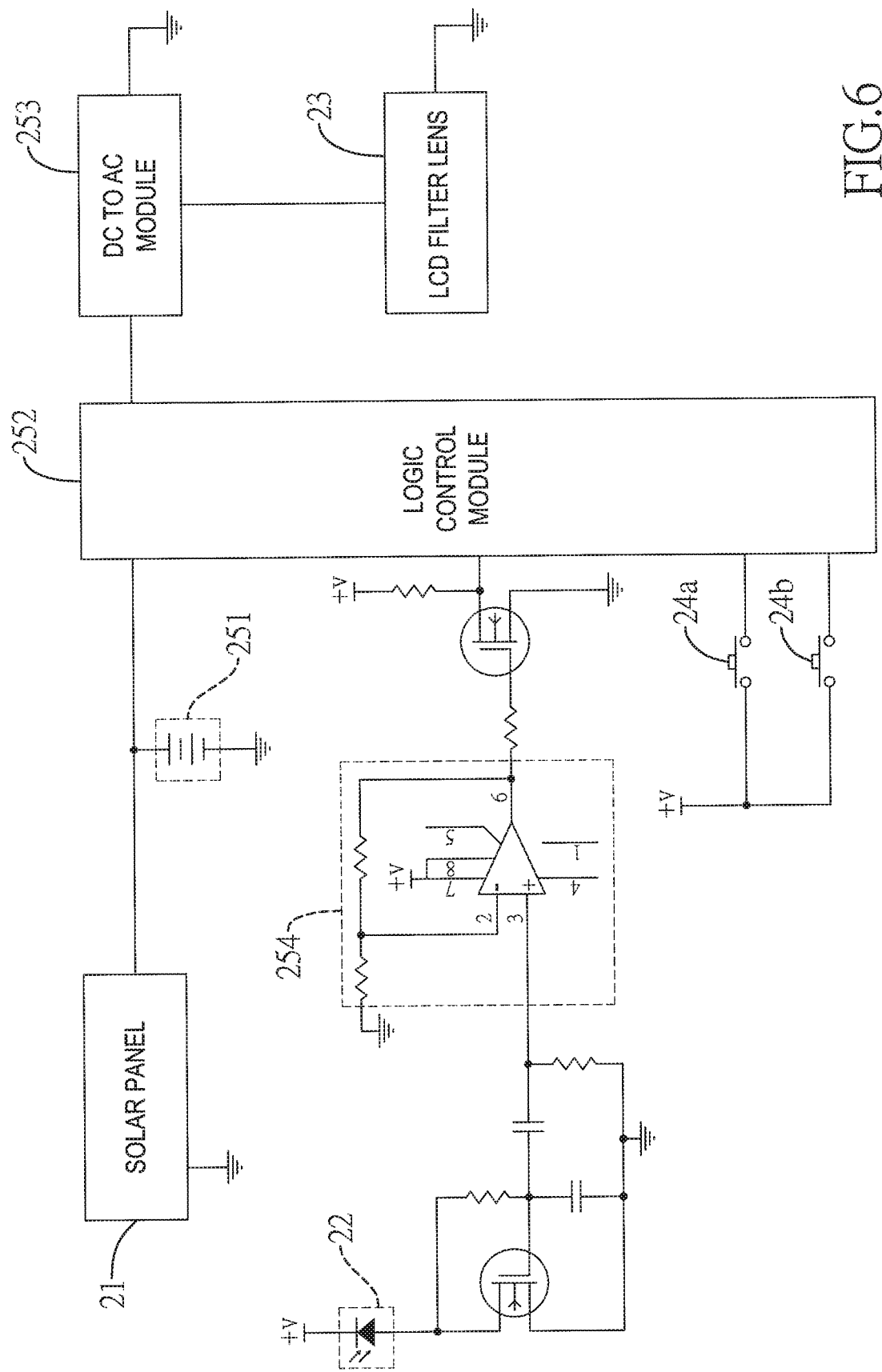
FIG. 6 is circuit diagram of the lens device.

With further reference to FIGS. 5 and 6, the filter control unit 25 is electrically connected to the solar panel 21, the light sensor 22 and the LCD filter lens 23. The filter control unit 25 includes a battery 251, a logic control module 252, a DC to AC module 253, an amplifier 254 and a regulating module 255.

The battery 251 is electrically connected to the solar panel 21 to receive and store the electric power and supplies the electric power to the logic control module 252, the light sensor 22, the amplifier 254 and the regulating module 255.

The DC to AC module 253 receives the electric power from the batter 251 for generating control signals.

The amplifier 254 is connected between the logic control module 252 and the light sensor 22. The amplifier 254 amplifies the light signal generated by the light sensor 22 and transmits the amplified light signal to the logic control module 252.

The regulating module 255 is connected between the logic control module 252 and the selection switches 24a, 24b.

The logic control module 252 is connected to the battery 251, the DC to AC module 253 and the amplifier 254 to receive the light signal and the shading-level signal. Based on the received light signal and the shading-level signal, the logic control module 252 controls the DC to AC module 253 to output different kinds of the control signals to control the LCD filer lens 23.

Figure 7A:
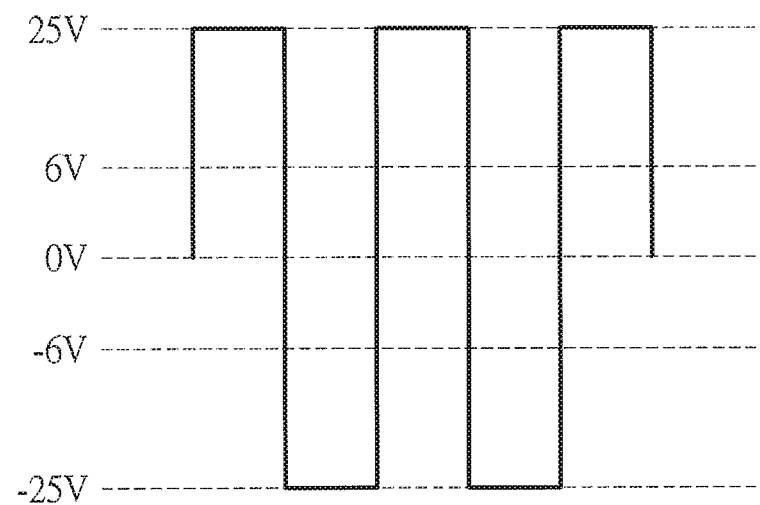
FIG. 7A shows a first control signal applied to the LCD panel for generating a high level shading effect.
Figure 7B:
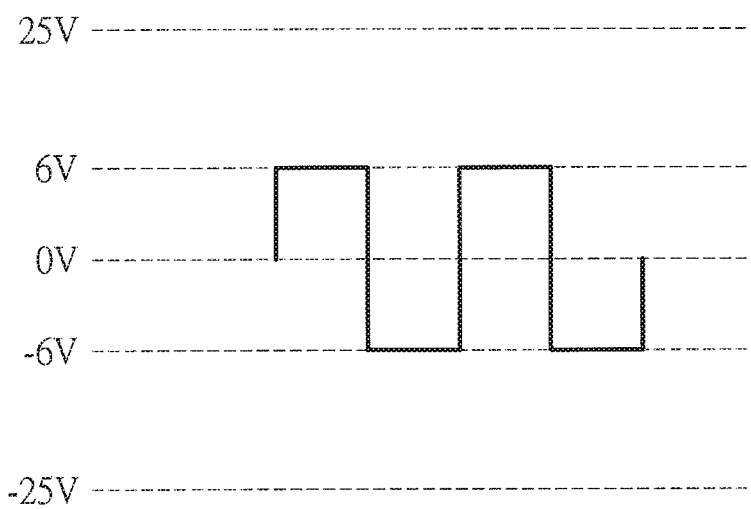
FIG. 7B shows a second control signal applied to the LCD panel for generating a low level shading effect.

With reference to FIGS. 7A and 7B, when the logic control module 252 determines that the light signal exceeds a threshold, the logic control module 252 controls the DC to AC module 253 to generate the control signals to activate the filter lens 23. The threshold can be determined in such a way as to ensure that the welding arc can be recognized when the sensed light signal is compared with the threshold.

The peak amplitudes of the control signals are determined by the shading-level signal generated by the first selection switch 24a or the second selection switch 24b. As shown in FIG. 7A, when the first selection switch 24 is pressed or activated by the user to generate the first shading-level signal, the DC to AC module 253 generates a first control signal having a relatively high peak amplitude such as 25 volts. When the first control signal is output to control the LCD panel 231, the LCD panel 231 turns dark to filter or block most ambient light or intense ambient light such as welding arcs. Therefore, the transmittance of the LCD panel 231 is at a low level to provide a high level shading effect, i.e. most ambient light will be filtered or blocked.

Alternatively, as shown in FIG. 7B, when the second selection switch 24b is pressed or activated by the user to generate the second shading-level signal, the DC to AC module 253 generates a second control signal having a relatively low peak amplitude such as 6 volts. When the second control signal is output to control the LCD panel 231, the LCD panel 231 also turns dark to filter or block part of the ambient light. However, the transmittance of the LCD panel 231 controlled by the second control signal is at a middle level to provide a low level shading effect, i.e. less ambient light will be filtered or blocked.

In another embodiment, when the lens device 20 has more switches, more shading-level signals may be generated by the multiple selection switches so that the LCD panel 231 can be controlled to provide more different levels of shading effects.

Figure 7C:
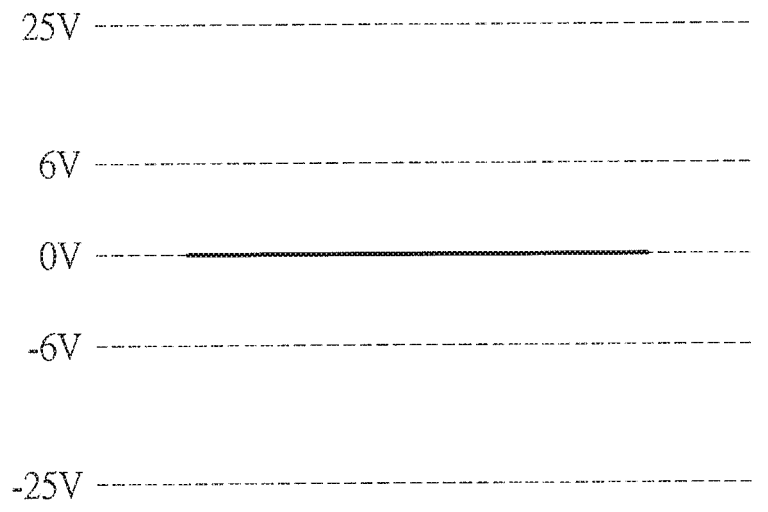

With reference to FIG. 7C, when the logic control module 252 determines that the light signal is lower than the threshold, a zero-voltage signal generated by the DC to AC module 253 is applied to the LCD panel 231. Regardless of the activation of the first selection switch 24a or the second selection switch 24b, the LCD panel 231 has the highest transmittance allowing ambient light to pass through. For example, the LCD panel 231 may become transparent when the zero-voltage signal is received.

According to one preferred embodiment, the amplitude of the control signals for driving the LCD panel 231 is controlled at between 6V and 25V, and the frequency of the control signals is in a range between 0.01 and 1 Hz, wherein a preferred frequency would be 0.1 to reduce flashing of the LCD panel 231. The control signals are alternating current (AC) square signals.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A welding helmet with a single liquid crystal display (LCD) filter lens, the welding helmet comprising:
   a helmet shell having a mounting hole; and
   a lens device fixed in the mounting hole of the helmet shell and comprising:
      a solar panel generating electric power;
      a light sensor generating a light signal corresponding to ambient light of the welding helmet;
      multiple selection switches for generating different shading-level signals respectively, wherein one of the multiple selection switches is selected to generate a designated shading-level signal;
      a filter control unit electrically connected to the solar panel, the light sensor and the multiple selection switches, and comprising:
         a battery connected to the solar panel and storing the electric power;
         a logic control module receiving the light signal and the designated shading-level signal and connected to the battery to receive the electric power; and
         a DC to AC module controlled by the logic control module to output a control signal; and
      a single LCD filter lens comprising a single LCD panel electrically connected to the DC to AC module and transmittance of the single LCD panel being determined by the control signal;
      wherein when the logic control module determines that the light signal is lower than a threshold, the DC to AC module outputs a zero-voltage signal and the single LCD panel is transparent;
      wherein when the logic control module determines that the light signal exceeds the threshold, the logic control module controls the DC to AC module to generate the control signal corresponding to the designated shading-level signal to lower the transmittance of the single LCD panel to a level for blocking the ambient light;
      wherein a peak amplitude of the control signal is between 6 and 25 volts and a frequency of the control signal is in a range between 0.01 and 1 Hz.

2. The welding helmet as claimed in claim 1, wherein the multiple selection switches comprise a first selection switch for generating a first shading-level signal and a second selection switch for generating a second shading-level signal;
- wherein when the first selection switch is selected, the control signal has a high peak amplitude to adjust the transmittance of the single LCD panel to a first level; and
- wherein when the second selection switch is selected, the control signal has a low peak amplitude to adjust the transmittance of the single LCD panel to a second level higher than the first level.

3. The welding helmet as claimed in claim 2, wherein the high peak amplitude is 25 volts and the low peak amplitude is 6 volts.

4. The welding helmet as claimed in claim 3, wherein the multiple selection switches are connected to the logic control module via a regulating module; and the light sensor is connected to the logic control module via an amplifier.

5. The welding helmet as claimed in claim 1, wherein the transmittance of the single LCD panel is determined according to a selected one of the different shading-level signals.

6. The welding helmet as claimed in claim 5, wherein the lens device has an outer surface and an inner surface; the solar panel and the light sensor are mounted on the outer surface; and the first switch and the second switch are mounted on the inner surface.

7. The welding helmet as claimed in claim 6, wherein the threshold is determined in such a way as to ensure that when a welding arc occurs, the light signal exceeds the threshold.

8. The welding helmet as claimed in claim 7, wherein the single LCD filter lens further comprises:
- an inner glass and an outer glass respectively attached to two opposite surfaces of the single LCD panel;
- the inner glass is a clear glass; and
- the outer glass is a reflective glass for reflecting ultraviolet radiation and infrared radiation of the welding arc.

9. The welding helmet as claimed in claim 8, wherein the control signal is an alternating current (AC) square signal.

\* \* \* \* \*